United States Patent [19]

Gereg

[11] 4,275,732
[45] Jun. 30, 1981

[54] SUCTION CANISTER WITH MEMBRANE SHUT-OFF VALVE

[76] Inventor: Gordon A. Gereg, P.O. Box 357, Center Valley,, Pa. 18034

[21] Appl. No.: 133,242

[22] Filed: Mar. 24, 1980

Related U.S. Application Data

[63] Continuation-in-part of Ser. No. 826,273, Aug. 19, 1977.

[51] Int. Cl.³ .............................................. A61M 1/00
[52] U.S. Cl. ........................... 128/276; 128/DIG. 24; 15/347
[58] Field of Search ....... 128/272, 275, 276, DIG. 24, 128/347

[56] References Cited

U.S. PATENT DOCUMENTS

| 3,575,170 | 4/1971 | Clark | 128/275 |
| 3,719,197 | 3/1973 | Pannier et al. | 128/276 |
| 3,814,098 | 6/1974 | Deaton et al. | 128/276 |
| 3,848,628 | 11/1974 | Deaton et al. | 137/434 |
| 3,998,255 | 12/1976 | Mather et al. | 128/295 |
| 4,004,590 | 1/1977 | Muriot | 128/276 |
| 4,111,204 | 9/1978 | Hessel | 128/276 |

FOREIGN PATENT DOCUMENTS 2329088  1/1975  Fed. Rep. of Germany .......... 128/275

OTHER PUBLICATIONS

"A Home Peritoneal Dialysate Delivery System", H. Tenckhoff et al., Trans. Amer. Soc. Artif. Int. Organs, vol. 15, pp. 103–107, 1969.

*Primary Examiner*—Kyle L. Howell
*Assistant Examiner*—J. L. Kruter
*Attorney, Agent, or Firm*—James H. Littlepage

[57] ABSTRACT

A flexible plastic bag is suspended from the lid of a rigid cylindrical vessel. In the side wall of the bag, near its top, is an aperture covered by a gas-permeable liquid-impermeable membrane. Suction is applied to space between the vessel and the bag so as to draw liquid into the bag. The membrane shuts off fluid flow therethrough when the liquid drawn into the bag covers the membrane. The lower portion of the vessel closely surrounds and supports the lower portion of the bag, whereas the upper portion of the vessel side wall is enlarged so as to provide clearance outwardly of the membrane.

1 Claim, 5 Drawing Figures

SUCTION CANISTER WITH MEMBRANE SHUT-OFF VALVE

RELATED APPLICATION

Gereg Ser. No. 826,273 filed Aug. 19, 1977 for Canister Assembly for Aspirating Body Liquids, of which this is a continuation-in-part.

FIELD OF INVENTION

Surgery, Aspirators.

PRIOR ART

Deaton U.S. Pat. No. 3,745,999; Fertig et al. U.S. Pat. No. 3,768,478; Hessel U.S. Pat. No. 4,111,204.

OBJECTS

Suction operated canisters, wherein liquid is collected in a flexible, disposable plastic bag have heretofore been provided with various filters and shut-offs designed to prevent body liquids collected in the bag from being drawn into the suction line. In Hessel (supra) a flexible plastic bag is suspended within a vessel and suction applied to space between the bag and the vessel draws air through a gas-permeable liquid impermeable membrane over an aperture near the top of the bag until the liquid level rises in the bag sufficiently to cover the membrane, whereupon all fluid flow through the membrane ceases. A major problem with this type of combined filter and shut-off results from the pressure differential between the interior of the bag and the surrounding space within the vessel. The interior of the bag is at or close to atmospheric pressure, whereas the surrounding space is at negative pressure which may be as high as 760 mm Hg. (14.7 psi). This tends to cause the bag to billow out and the stresses may cause the bag to burst along a seam or at a weak point, or they may cause a seal between the bag top and the vessel top or the seal between the membrane and the bag to fail.

While, ideally, it would appear expedient to support the bag in its entirety by closely matching the size of the vessel to the desired distended size of the bag, this is impractical because as the bag expands, the membrane presses against the inner side wall of the vessel and this can cause a pressure drop between the interior of the bag and the bag exterior. Thus the eduction of body fluid from the patient ceases, the bag is unnecessarily stressed, and there is created a false "bag full" signal in a pressure-sensitive device in the suction line. The object of this invention is to so shape the vessel as to provide the maximum practical support for the bag exterior, yet still providing clearance outwardly of the membrane. To this end it is intended now to provide a cylindrical vessel with an upper side wall portion which is enlarged with respect to a lower side wall portion. A further object is to provide a curved transition between the upper and lower portions of the vessel so as to facilitate insertion of the bag into the vessel.

Still another object is to provide a membrane covered aperture which is rectangular and elongate in the circumferential direction of the bag. The objects in connection with this shape are:

(a) to provide the maximum practical length of the seal between the membrane and the bag for a given area of the membrane and thereby to maximize the distribution of the stresses between the membrane and the bag;

(b) to provide for a gradual increase in the pressure drop across the membrane as the liquid level rises towards the top of the aperture, and then to provide a sharp increase in the pressure drop as the liquid level reaches the upper edge of the aperture so as to create an easily detectable "bag full" signal in the suction line; and (c) to minimize the span across the unconfined portion of the bag, i.e., the span between where the bag is closely confined by the vessel and where the bag is attached into the vessel lid.

These and other objects will be apparent from the following specification and drawing, in which.

Figure 1:
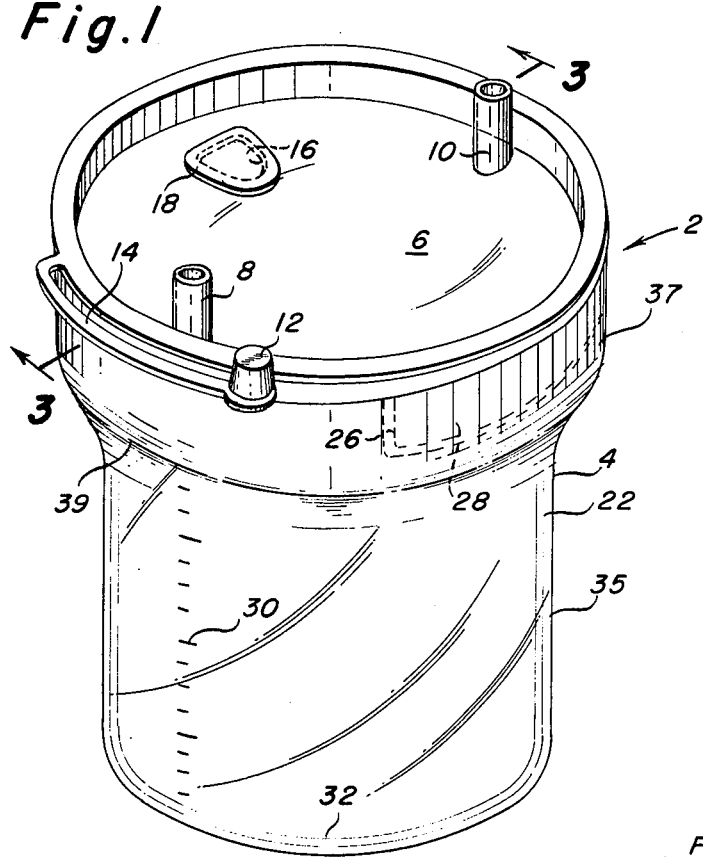
FIG. 1 is a perspective view of the canister.
Figure 4:
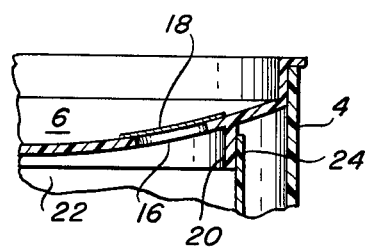
FIG. 4 is a fragmentary cross-section illustrating the detail of the lid.
Figure 3:
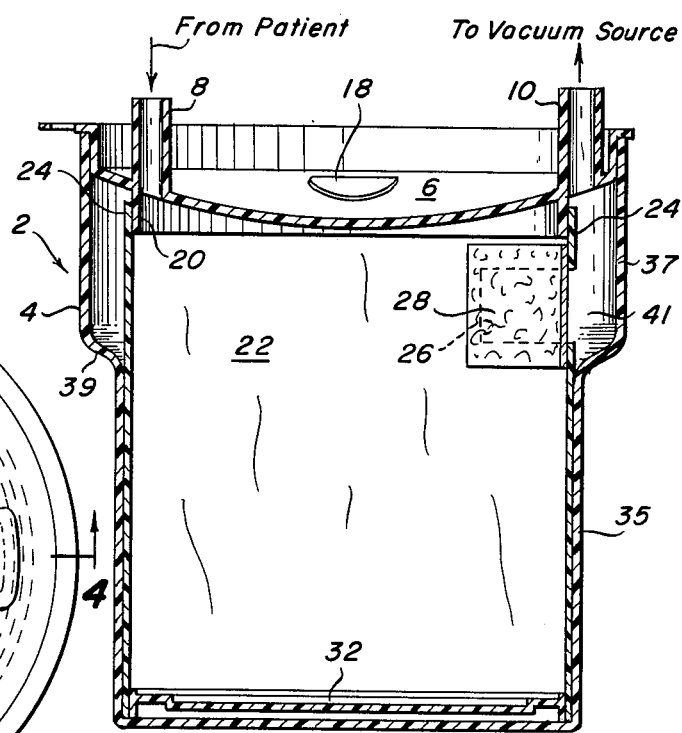
FIG. 3 is a vertical cross-section through the canister.
Figure 2:
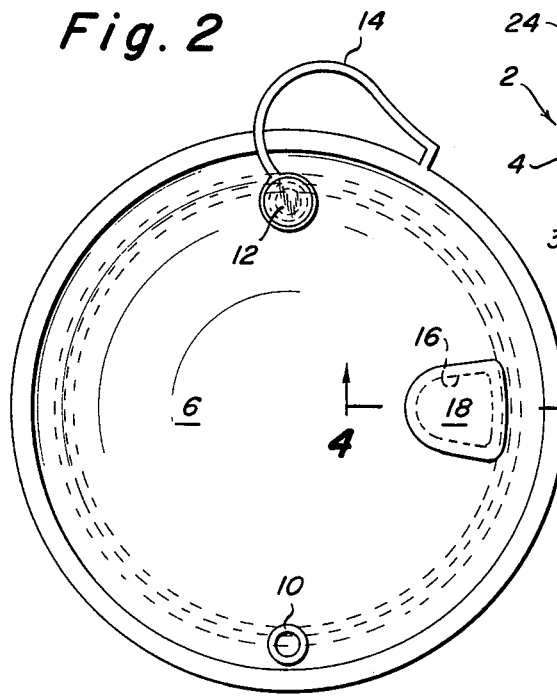
FIG. 2 is a plan view of the canister.

Referring now to the drawing in which line reference numerals denote similar elements, the canister 2 comprises a cylindrical vessel 4 having a removable lid 6 with upstanding nipples 8 and 10 which are tube couplings, the nipple 8 being for coupling to a tube leading from the patient from whom liquid is to be drained and the nipple 10 for coupling to a tube leading to a vacuum pump or tank. Nipple 10 is disposed somewhat closer to the periphery of the lid than is tube 8. A plug 12 for closing one of the nipples is held captive to the lid by a tether 14. The lid is also provided with a port 16, for quick bag emptying, which port is normally closed by a tape patch 18, and a depending flange 20 which lies inside the open lower end of nipple 10 and outside the open lower end of nipple 8.

Figure 5:
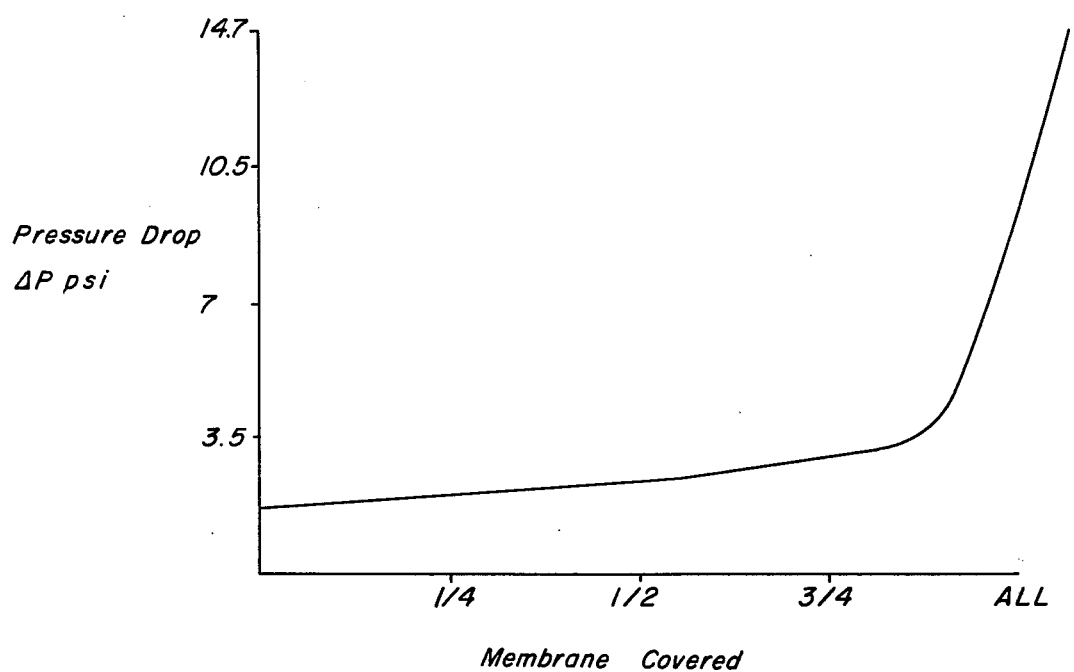
FIG. 5 is a graph of the pressure drop across the membrane plotted against the portion of the membrane covered by liquid in the canister.

Suspended within vessel 4 is a plastic bag 22 having a flexible side wall 24 whose upper edge is sealed around flange 20 by suitable means such as a heat seal. The bag side wall has through it, near its top, an aperture 26 which is covered by a membrane 28 secured, as by heat sealing, to the inner side of the bag side wall. A membrane of this type is presently marketed by W. L. Gore and Associates of Elkton, Md. under the name of "Gore-Tex". Because of the flimsy nature of the membrane, it is laminated onto a sub-strate, such as "Webril" a product of Kendall Company, Walpole, Mass., an expanded polypropylene sealable to the bag material. The essential characteristics of the laminate are that it will pass gas, such as air, but will not pass liquids, such as water and body liquids, and that it is impermeable to bacteria larger than 0.5 micron. Thus, most common infectious materials will not pass out of the bag. While other aperture shapes are operative, the best shape is that of a rectangle which is elongate in the circumferential direction of the bag. With this aperture shape, a gradual cut off of the air flow to the vacuum side of the system is achieved as the liquid level rises across the membrane. However, as the liquid level approaches the top of the aperture, a sharp-off signal is produced in the suction line, i.e., the vacuum in the line suddenly increases. FIG. 5 is a graph of the pressure drop across the membrane plotted against the portion of the membrane covered by liquid within the canister. This shape also provides the maximum length for the seal between the membrane and the bag for a given area of membrane and it also achieves a further advantage described below.

Both the bag and the vessel have cylindrical side walls. The vessel has a lower portion 35 whose inner diameter is approximately equal to the outer diameter of the bag 22 so that the bag fits snuggly therein. The upper portion 37 of the vessel side wall is enlarged and is connected to the lower portion by a curved transition 39. The enlarged upper portion of the vessel side wall provides a clearance space 41 exteriorly of the membrane 28.

The curved transition 39 facilitates insertion of the bag into the vessel and provides a surface which does not rupture or tear the bag as the latter presses against it, particularly at the lower portion of the transition. The clearance space 41 assures that the membrane cannot engage against the inner side of the side wall of the vessel and thereby shut off the eduction of body fluid from the patient and also create a sudden pressure drop in the suction line which would give a false "bag full" signal or produce unnecessary stresses in the bag material.

Because the interior of the bag is at atmospheric pressure and because fluid flow through the membrane is blocked when the liquid completely masks it, the space between the bag and the canister is subjected to such negative pressure, as high as 760 mm Hg (14.7 psi) that the bag, unless otherwise supported, tends to billow out and rupture, particularly at any weak point. The rectangular, circumferentially elongate shape of the aperture minimizes the unconfined area of the bag, i.e., the span between the curved transition 39 and the flange 20 to which the top of the bag is sealed. To accomplish this, the distance between the upper and lower edges of the rectangle in the axial direction of the bag should be at least as great as the major portion of the span across the upper portion of the vessel in the axial direction thereof, i.e., between the top of the lower portion of the vessel and the top of the upper portion.

In a typical example, the measurements are as follows:

Axial length of bag 22=6¾ inches
Inside axial length of vessel 4=7 inches
Normal diameter of bag 22 when full=5 inches
Inside diameter of lower portion 35 of vessel=5¼ inches
Inside diameter of upper portion 37 of vessel=6 inches
Inside axial length of lower portion 35 of vessel to start of transition=4½ inches
Inside axial length of upper portion 37 of vessel from transition to top=2 inches
Inside axial length of curved transition 39=⅜ inch
Length of aperture 26 in circumferential direction of bag=6¾ inches
Length of aperture 26 in axial direction of bag=1 inch.

The curve of FIG. 5 was plotted for a membrane of the size, shape and orientation as in the foregoing example.

In the development of the data from which the curve of FIG. 5 was plotted, there were taken into account certain fundamentals as follows:

Pressure drop for a viscous fluid or gas through an orifice is dependent on viscous forces and inertia or turbulence effects. A common index of flow characteristics is the Reynolds number which is a ration of the inertia forces for a given fluid flowing through a certain size orifice at varying velocities. A critical Reynolds number can be determined above which the inertia forces become predominant and the pressure drop is proportional to the kinetic energy of the stream which increases as the square of the velocity. Below the critical Reynolds number the pressure drop is directly proportional to the velocity. Because the membrane has a mass of small orifices of indeterminate size and shape, a Reynolds number cannot be accurately calculated but the effect can be experimentally seen.

For this application it can be assumed that the membrane is the controlling element since the patient connection and the tubing are free flowing enough to overtake the flow capacity of the membrane. There can be an effect caused by the pump capacity but it can be assumed that this merely displaces the curve without affecting its shape. As the pressure drop increases, there is a reservoir of vacuum (which is a store of kinetic energy) in the bag head space. As the area available for gas flow decreases, the velocity increases, adding to the steepness of the final portion of the pressure drop curve where the pressure drop varies as the square of the velocity.

For practical purposes, the critical break point can be said to be at a level where ¾ of the membrane is covered. Up to the halfway point, the change in flow characteristics or the pressure drop, may not be enough for a user or a sensing device to detect.

I claim:

1. A canister for use in aspirating body liquids, comprising
   a circular cylindrical vessel substantially closed to the atmosphere with top and bottom closures,
   a flexible plastic bag of fluid-impermeable material having upper and lower side wall portions which are normally circularly cylindrical when the bag is fully distended
   means for suspending said bag from the top closure within said vessel with the axis of the bag vertically disposed,
   a generally rectangular aperture through the upper side wall portion of the bag adjacent to top thereof, said aperture being substantially longer in the circumferential direction of the bag side wall than in the axial direction thereof and being bounded at its top and bottom by edges which extend in the circumferential direction of the bag,
   a first fluid coupling means for connecting the interior of said bag to a liquid withdrawal conduit extending exteriorly of the cannister,
   a second fluid coupling means for connecting space between the exterior of said bag and the interior of said vessel to a source of vacuum,
   a liquid impermeable, gas permeable membrane across said aperture,
   said vessel having lower and upper cylindrical side wall portions of relatively lesser and greater diameters respectively connected by a transitional portion which extends outwardly and upwardly from the top of the lower side wall portion of the vessel to the bottom of the upper side wall portion of the vessel, the upper side wall portion of the vessel being disposed laterally outward from the upper side wall portion of the bag,
   the relative sizes of the side wall portions of the vessel and bag being such that when the bag is fully distended the lower side wall portion of the vessel closely and supports the lower side wall portion of the bag, and the upper side wall portion of the vessel is spaced outwardly from the upper side wall portion of the bag, whereby the vessel provides support of the lower side wall portion of the bag against outward distortion and the upper portion of the vessel provides clearance outwardly of the membrane so as to avoid masking thereof as the bag fills.

* * * * *

UNITED STATES PATENT AND TRADEMARK OFFICE
CERTIFICATE OF CORRECTION

PATENT NO. : 4,275,732
DATED : June 30, 1981
INVENTOR(S) : Gordon A. Gereg

It is certified that error appears in the above—identified patent and that said Letters Patent is hereby corrected as shown below:

In column 3, line 61, delete "ration",
        insert --ratio--.
In column 4, line 59, after "closely",
        insert --surrounds--.

Signed and Sealed this

Twenty-third Day of February 1982

[SEAL]

Attest:

GERALD J. MOSSINGHOFF

Attesting Officer     Commissioner of Patents and Trademarks